(12) United States Patent
Lee et al.

(10) Patent No.: US 7,545,510 B2
(45) Date of Patent: Jun. 9, 2009

(54) METHOD OF CHARACTERIZING TRANSPARENT THIN-FILMS USING DIFFERENTIAL OPTICAL SECTIONING INTERFERENCE MICROSCOPY

(75) Inventors: Chau-Hwang Lee, Taipei County (TW); Chun-Chieh Wang, Da-Li (TW)

(73) Assignee: Academia Sinica, Nan-Kang, Taipei (TW)

( * ) Notice: Subject to any disclaimer, the term of this patent is extended or adjusted under 35 U.S.C. 154(b) by 0 days.

(21) Appl. No.: 11/789,769

(22) Filed: Apr. 25, 2007

(65) Prior Publication Data
US 2008/0266548 A1 Oct. 30, 2008

(51) Int. Cl.
*G01B 11/02* (2006.01)
(52) U.S. Cl. .................... 356/503; 356/517
(58) Field of Classification Search .............. 356/503, 356/504, 517, 484–486, 630, 632
See application file for complete search history.

(56) References Cited

U.S. PATENT DOCUMENTS 5,804,813 A 9/1998 Wang et al.
6,370,422 B1 * 4/2002 Richards-Kortum et al. 600/478

OTHER PUBLICATIONS

Wang et al., "Transparent thin-film characterization by using differential optical sectioning interference microscooy", *Applied Optics*, vol. 46, No. 30 (2007).

Tsai et al., Deconvolution of local surface response from topography in nanometer profilometry with a dual-scan method, *Optics Letters* vol. 24, No. 23 (1999).
Liu et al., Image scanning ellipsometry for measuring nonuniform film thickness profiles, *Applied Optics*, vol. 33 No. 7 (1994).
Otsuki et al., Two-dimensional thickness measurements based on internal reflection ellipsometry, *Applied Optics* vol. 44, No. 8 (2005).
Neil et al., Method of obtaining optical sectioning by using structured light ina conventional microscope, *Optics Letters* vol. 22, No. 24 (1997).
Lee et al., Noninterferometric differential confocal microscopy with 2-nm depth resolution, *Optics Communications* 135 (1997) p. 233-237.
Lee et al., Noninterferometric wide-field optical profilometry with nanometer depth resolution, *Optics Letter*, vol. 27, No. 20 (2002).
Wang et al., Membrane ripples of a living cell measured by non-interferometric widefield optical protilometry, *Optics Express* vol. 13, No. 26 (2005).

(Continued)

*Primary Examiner*—Hwa S Lee
*Assistant Examiner*—Jonathon D Cook
(74) *Attorney, Agent, or Firm*—Cohen Pontani Lieberman & Pavane LLP

(57) ABSTRACT

An imaging, differential optical sectioning interference microscopy (DOSIM) system and method for measuring refractive indices and thicknesses of transparent thin-films. The refractive index and thickness are calculated from two interferometric images of the sample transparent thin-film having a vertical offset that falls within the linear region of an axial response curve of optically sectioning microscopy. Here, the images are formed by a microscope objective in the normal direction, i.e., in the direction perpendicular to the latitudinal surface of the thin-film. As a result, the lateral resolution of the transparent thin-film is estimated based on the Rayleigh criterion, $0.61\lambda/NA$.

36 Claims, 6 Drawing Sheets

OTHER PUBLICATIONS

A. Albersdorfer, G. Elender, G. Mathe, K. R. Neumaier, P. Paduschek, and E. Sackmann, "High resolution imaging microellipsometry of soft surfaces at 3 μm lateral and 5 Å normal resolution," Appl. Phys. Lett. 72, 2930-2932 (1998).

Q. Zhan and J. R. Leger, "High-resolution imaging ellipsometer," Appl. Opt. 41, 4443-4450 (2002).

F. Linke and R. Merkel, "Wuantitative ellipsometric microscopy at the silicon-air interface", Review of Scientific Instruments 76, 063701 (2005).

Chun-Chieh Wang et al., Transparent thin-film characterization by using differential optical sectioning interference microscopy, Abstract (2007).

* cited by examiner

METHOD OF CHARACTERIZING TRANSPARENT THIN-FILMS USING DIFFERENTIAL OPTICAL SECTIONING INTERFERENCE MICROSCOPY

BACKGROUND OF THE INVENTION

1. Field of the Invention

The present invention relates to transparent thin-films and, more particularly, to an imaging, differential optical sectioning interference microscopy (DOSIM) system and method for measuring refractive indices n and thicknesses d of transparent thin-films.

2. Description of the Related Art

Refractive indices (n) and thicknesses (d) of thin-films are essential parameters for modern electronic and optoelectronic devices. At present, ellipsometers are the preferred tool for measuring refractive indices and thicknesses of transparent thin-films.[1] Such conventional ellipsometers use an obliquely incident light path to illuminate the specimens films. However, the geometry associated with such conventional ellipsometers tends to increase the lateral resolution of the measurement in the order of larger than tens of micrometers.

A variety of imaging ellipsometers have been developed to improve the lateral resolution for thin-film characterizations.[2-4] However, the optical geometry of inclined illumination or obliquely illuminated light path still renders the lateral resolution in the order of a few micrometers. Another recent proposed solution for achieving sub-micrometer lateral resolution involved the use of a high-resolution imaging ellipsometer using a high numerical aperture (NA) microscope objective as a probe.[5] However, such a proposed solution does not indicate that the simultaneous measurement of n and d of inhomogeneous thin-films can be achieved. In view of the foregoing, it is apparent there is a need for a method and system for measuring refractive indices (n) and thicknesses (d) of transparent thin-films.

SUMMARY OF THE INVENTION

An imaging, differential optical sectioning interference microscopy (DOSIM) system and method for measuring refractive indices n and thicknesses d of transparent thin-films. The refractive index and thickness are calculated from two interferometric images of the sample transparent thin-film having a vertical offset that falls within the linear region of the axial response curve of optically sectioning microscopy.

The method and DOSIM system combines three principles: wide field optical sectioning microscopy,[6] differential confocal microscopy,[7] and Fabry-Perot interferometry within a simple setup based on a conventional optical microscope. As stated, the images are formed through the microscope objective in the normal direction, i.e., in the direction perpendicular to the latitudinal plane of the thin-film. As a result, the lateral resolution of the transparent thin-film is determined in a simple manner based on the Rayleigh criterion, i.e., $0.61\lambda/NA$, where $\lambda$ is the illumination wavelength of the light, and NA is the numerical aperture of the objective. The DOSIM system of the invention does not rely on the polarization of light, and therefore the system is easy to construct and calibrate.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The foregoing and other advantages and features of the invention will become more apparent from the detailed description of the preferred embodiments of the invention given below with reference to the accompanying drawings in which.

DETAILED DESCRIPTION OF THE PRESENTLY PREFERRED EMBODIMENTS

Figure 1:
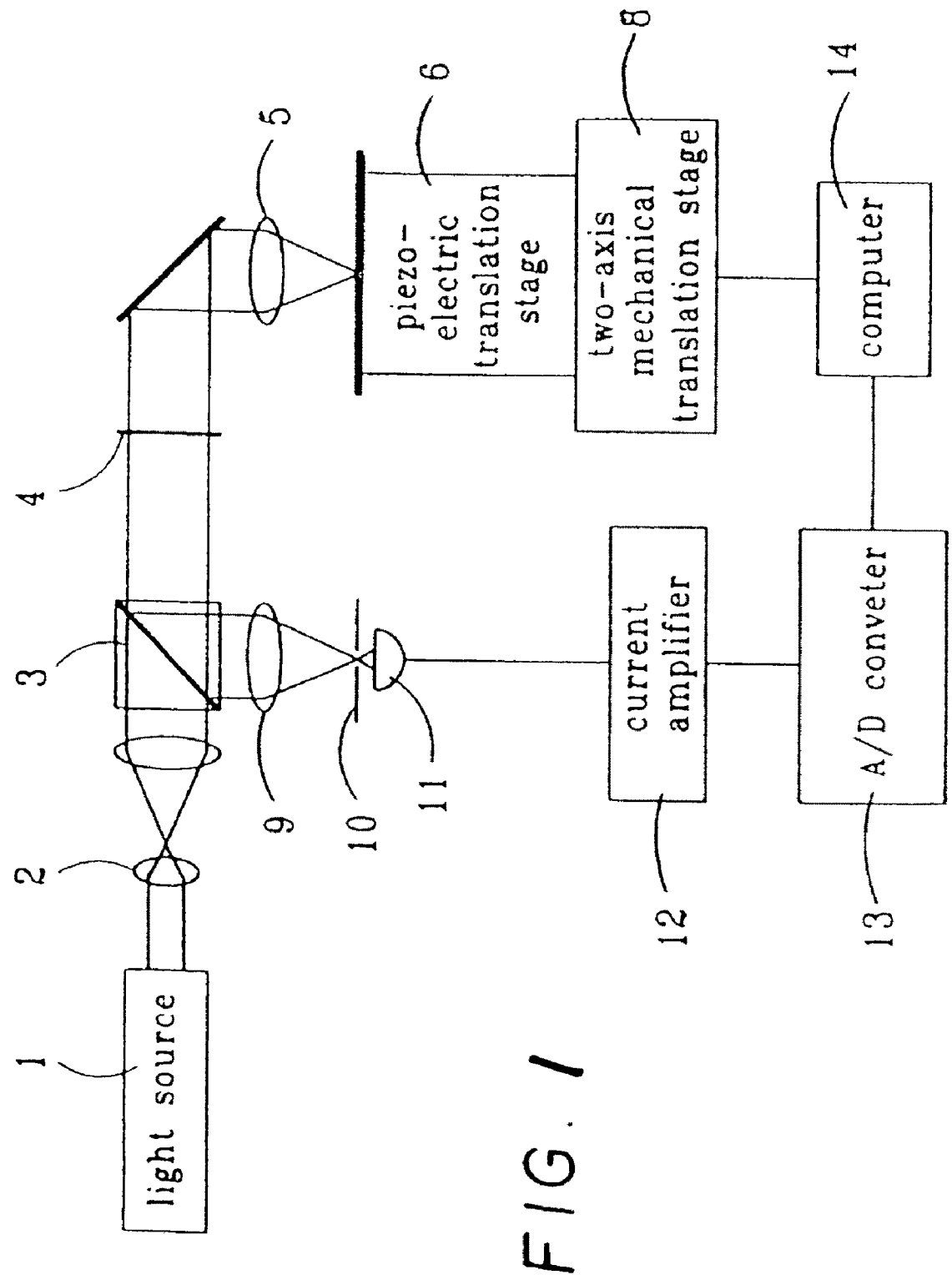
FIG. 1 is an illustration of an exemplary "differential confocal microscopy".

FIG. 1 is an illustration of an exemplary "differential confocal microscopy". Such a system is described in detail in U.S. Pat. No. 5,804,813, the contents of which are incorporated herein in its entirety. With reference to FIG. 1, light source 1 emits a beam through a beam expander 2, and the beam is then focused by the focusing device 5 onto a sample which is at the top of a piezo-electric translator (PZT) 6. The sample is put on the PZT 6, and the PZT 6 is set up on computer-controlled two-axis mechanical translation stages 8. Before performing measurements, the distance between the sample is adjusted, and the focusing device 5 is adjusted to the focal length of the focusing device by maximizing the detected signal, and the PZT 6 is adjusted to move the sample to the linear slope region of the axial response curve of confocal microscopy, which is the working range of the present "differential confocal microscopy" of the present invention.

The two-axis mechanical translation stage 8 is for two dimensional scanning of the sample in the plane transverse to the propagation direction of the light beam, and may alternatively be in the form of piezo-electric translation stages, electromagnetic translation stages. Still further scanning may be achieved by using acousto-optic or electro-optic modulators, or rotational or vibrational optical scanners which may use reflective mirrors, refractive lenses, prisms, or diffraction devices such as gratings to change the direction of the beam relative to the surface.

Because the feedback light will interfere with the light inside the laser cavity, a polarization beam splitter 3 with a quarter wave plate 4 are used in the optical path to eliminate the interference, although feedback could be provided by the light source itself if the light source is affected by the confocal feedback light and changes its own characteristics in direct proportion to feedback light intensity. The reflected light from the sample surface goes through the polarization beam splitter 3 and is almost completely reflected to an optical detector 11, which can use photodiodes, avalanche photodiodes, photo multipliers, charge coupled devices (CCDs), or fluorescent screens; where it passes the spatial filter which is composed by another focusing device 9 and a pinhole 10. The signal is detected by the optical detector 11 and then amplified by a signal amplifier 12. The amplified signal is recorded by an analog-to-digital converter 13, and then stored by a computer 14 for the generation of images.

FIG. 2(*a*) is a schematic block diagram of a differential optical sectioning interference microscopy (DOSIM) system in accordance with the present invention. With reference to FIG. 2(*a*), the light source 1 is used to provide a signal light, such as a power-regulated mercury-xenon lamp equipped with a 3-nm-bandwidth interference filter 4 centered at 600 nm. A 50× microscope objective having a 0.55 numerical aperture (NA) is used to collect the signal light, and thus provide a lateral resolution of about 0.67 µm. With additional reference to FIG. 2(*a*), images are captured by a camera 15, such as a 14-bit CCD camera cooled at −25° C. With such a setup, the field of view of the captured images is around 230×170 µm². In the disclosed DOSIM system, a grid pattern is projected onto a sample transparent thin-film in the form of a synthesized aperture to produce optical sectioning.[6] It should be appreciated that different grid patterns may be used. In the instant invention, one such pattern can be a 200 cycle/inch grid pattern. Here, the spatial frequency of the grid pattern that is projected onto the sample thin-film is 0.46 µm$^{-1}$. In accordance with the invention, optical sectioning is achieved when three images ($I_1$, $I_2$, $I_3$) with the grid pattern at spatial phases of 0, $2\pi/3$, and $4\pi/3$ are captured and processed in accordance with the homodyne detection principle, which provides that $I_s = \sqrt{(I_1-I_2)^2+(I_2-I_3)^2+(I_1-I_3)^2}$. Homodyne detection is a method of detecting frequency-modulated radiation by non-linear mixing with radiation of a reference frequency.

Figure 3:
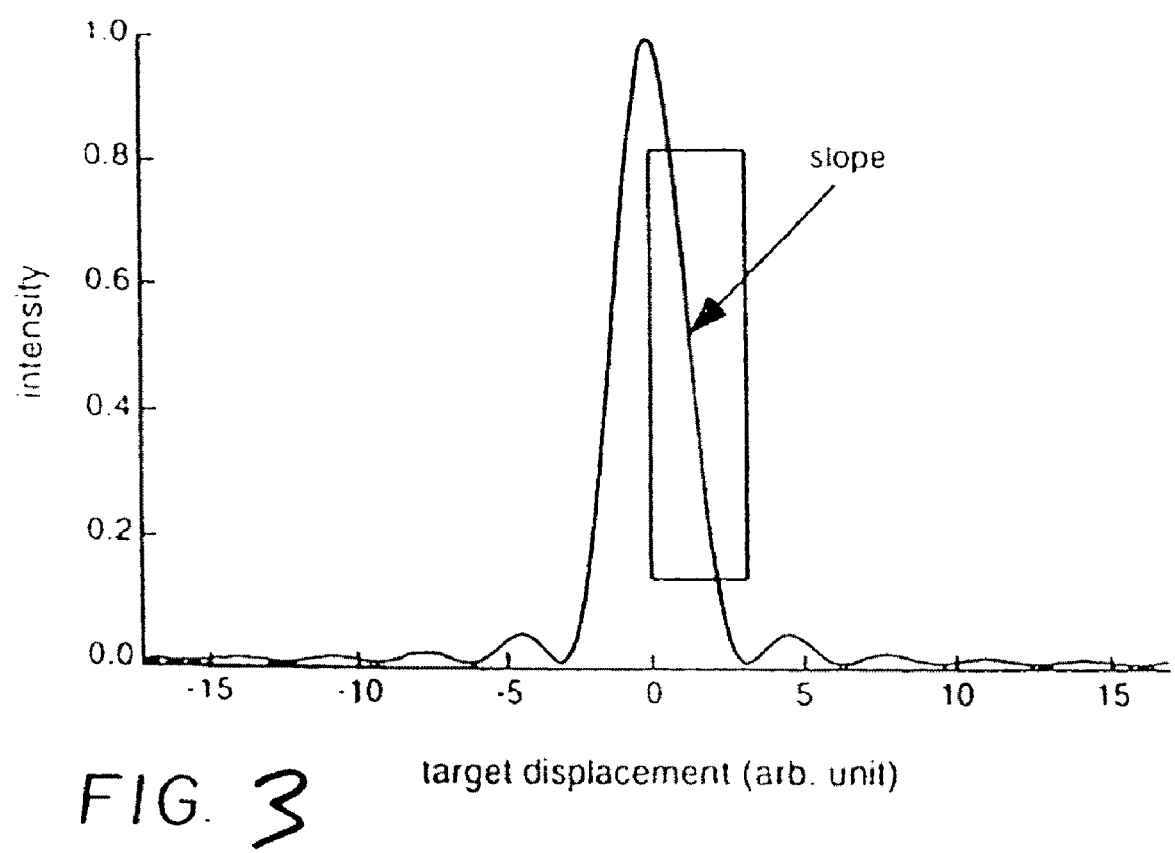
FIG. 3 is a graphical plot of the relationship between the signal intensity and the axial displacement of a sample in confocal microscopy, where the square indicates the linear slope region.

Optical sectioning in this manner provides an axial response curve that is similar to the axial response curve obtained by confocal microscopy. Therefore, as the surface of the sample is placed into the linear region of the axial response curve, height variations cause significant signal differences. As shown in FIG. 3, the relationship between the signal intensity and the axial displacement of the sample is approximately a sinc² curve in confocal microscopy. The maximum of this sinc² curve corresponds to the focal point of the detecting microscope objective lens. Although the signal is maximal at the focal point, the derivative of signal intensity versus the displacement of the sample is zero. Consequently, at this position, the confocal signal is insensitive to the sample displacement. In particular, when the signal light comes from the sample surface, placing the sample at the focal point cannot obtain high depth resolution. Upon adjusting the height of the sample such that its surface is in the linear slope region of the sinc² curve, i.e., resides with the square shown in the graphical plot of FIG. 3, the axial displacement of the sample causes a differential change in the signal intensity. In this region, the signal intensity is very sensitive to small changes in the surface height, and therefore the depth resolution can be greatly increased. Further details of differential confocal microscopy are described in U.S. Pat. No. 5,804,813, which is incorporated herein in its entirety.

FIG. 2(*b*) is a graphical plot illustrating the linear region of the axial response curve of the DOSIM system of FIG. 2(*a*). Here, the slope ($\alpha$) of the fitting straight line is 1.03 µm$^{-1}$. In accordance with the invention, nanometer depth resolution can be achieved after calibrating the height-intensity response curve. The present inventors have verified the associated principles using the above described differential confocal microscopy.[7] The present inventors have also demonstrated the feasibility of wide-field differential sectioning microscopy on solid-state[8] and biological specimens.[9]

In accordance with the present invention, the index and thickness of the transparent thin-film are calculated in accordance with the following process. Here, an assumption is made that the transparent thin-film is exposed to monochromatic illumination in the normal direction. Taking the Fabry-Perot interferometric effect into account, a reflection signal is obtained in accordance with the following relationship:

$$I_r(n_2, d) \propto \left| E_0 e^{j\omega t} \left[ r_1 + \frac{(1-r_1^2)r_2 e^{-j\delta}}{1+r_1 r_2 e^{-j\delta}} \right] \right|^2 \quad \text{Eq. 1}$$

$$\propto I_0 \left( \frac{|r_1|^2 + r_1 r_2^* e^{j\delta} + r_1^* r_2 e^{-j\delta} + |r_2|^2}{1+r_1^* r_2^* e^{j\delta} + r_1 r_2 e^{-j\delta} + |r_1|^2|r_2|^2} \right),$$

where $I_r$ is the measured intensity, $E_0$ and $I_0$ is the incident electric field and light intensity, $\delta(n_2, d) = 4\pi n_2 d/\lambda_0$ with the $\lambda_0$ illumination wavelength in air. $r_1$ and $r_2$ are the reflection coefficients of electric field on the air/thin-film and thin-film/substrate interfaces, respectively. Here, $n_2$ and d represent the refractive index and thickness of thin-film. In the case that d is smaller than the focal depth of the microscope objective, $r_1$ and $r_2$ can be obtained in accordance with the following relationship:

$$r_{1,2}(n_2) = (n_{1,2}-n_{2,3})/(n_{1,2}+n_{2,3}), \quad \text{Eq. 2}$$

where $n_1$ and $n_3$ are the refractive indices of air and the substrate. Both $n_1$ and $n_3$ are determined before the measurement.

Figure 2A:
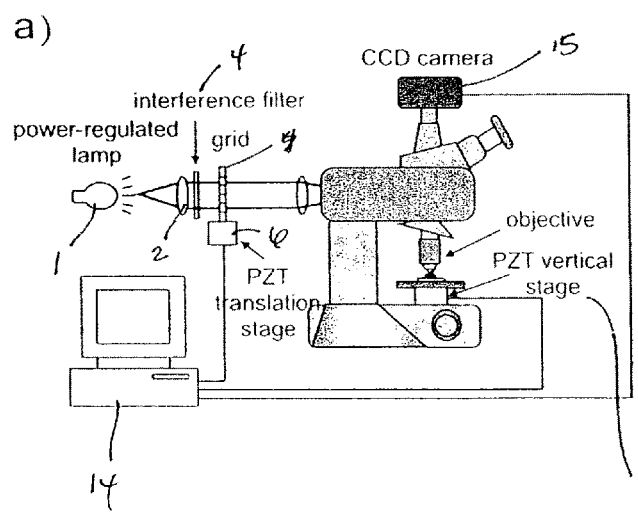
FIG. 2(a) is a schematic block diagram illustrating a differential optical sectioning interference microscopy (DOSIM) system in accordance with the invention.
Figure 2B:
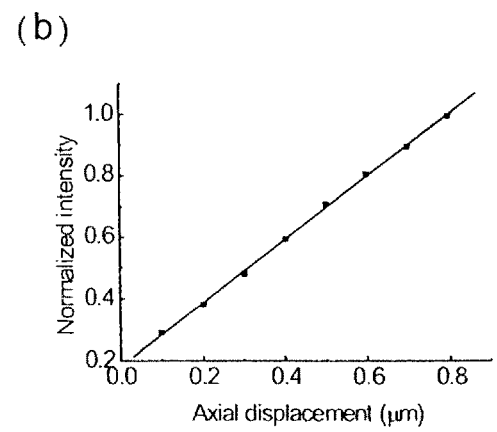
FIG. 2(b) is a graphical plot illustrating the linear region of the axial response curve of the DOSIM system of FIG. 2(a)

As the thin-film is placed into the linear region of the axial response curve of optical sectioning microscopy, the relationship expressed in Eq. 1 becomes expressed in accordance with the following relationship:

$$I_{DOSIM}(n, d) \propto \left| E_0 e^{j\omega t} \left[ r_1 T_1 + \frac{(1-r_1^2)r_2 e^{-j\delta}}{1+r_1 r_2 e^{-j\delta}} T_2 \right] \right|^2 \quad \text{Eq. 3}$$

$$\propto I_0 \left( \frac{|r_1|^2 T_1^2 + r_1 r_2^* T_1 T e^{j\delta} + r_1^* r_2 T_1 T e^{-j\delta} + |r_2|^2 T^2}{1+r_1^* r_2^* e^{j\delta} + r_1 r_2 e^{-j\delta} + |r_1|^2|r_2|^2} \right),$$

where $T_1$ and $T_2$ are the effective transmission coefficient of the electric field that is generated by the synthesized sectioning aperture at the air/thin-film and thin-film/substrate interfaces, and $T=r_1^2 T_1+(1-r_1^2)T_2$. In the linear region, it is possible to express $T_1$ and $T_2$ in accordance with the relationships:

$$T_1=\sqrt{\alpha(Z_{sub}+d)}, \text{ and} \qquad \text{Eq. 4}$$

$$T_2=\sqrt{\alpha[Z_{sub}+(1-n_1/n_2)d]}, \qquad \text{Eq. 5}$$

where α is the slope of the linear response curve illustrated in FIG. 2(b) and $Z_{sub}$ is the position of the substrate surface relative to the origin of the displacement axis in FIG. 1(b). Here, the term $(1-n_1/n_2)d$ in $T_2$ accounts for the vertical shift of the substrate image under the transparent thin-film. The position of the PZT vertical stage is then recorded pursuant to obtaining the graphical plot illustrating the linear region of the axial response curve shown in FIG. 2(b), during which the values of $Z_{sub}$ and α are known. As a result, the only values that are unknown in Eq. (3) are $n_2$ and d.

The parameters $n_2$ and d, i.e., the refractive indices and thicknesses, are derived by solving the relationship described in the two independent relationships set forth in Eq. 2. Such independent equations may be obtained by acquiring multiple images while the sample thin-film is placed at multiple positions along the optical axis of the light.[10] In the preferred embodiment, two images and two positions along the optical axis are acquired, i.e., two different values of $Z_{sub}$ are acquired. In an embodiment, an average of multiple images acquired at each vertical position as the measured $I_{DOSIM}$ of Eq. (3) can be used to increase the signal-to-noise ratio. In the preferred embodiment, an average of 9 images at each vertical position is used. Here, the vertical offset between the two vertical positions provided by the PZT vertical stage is 300 nm. Finally, the values of $n_2$ and d are obtained by solving the two equations numerically.

Figure 4:
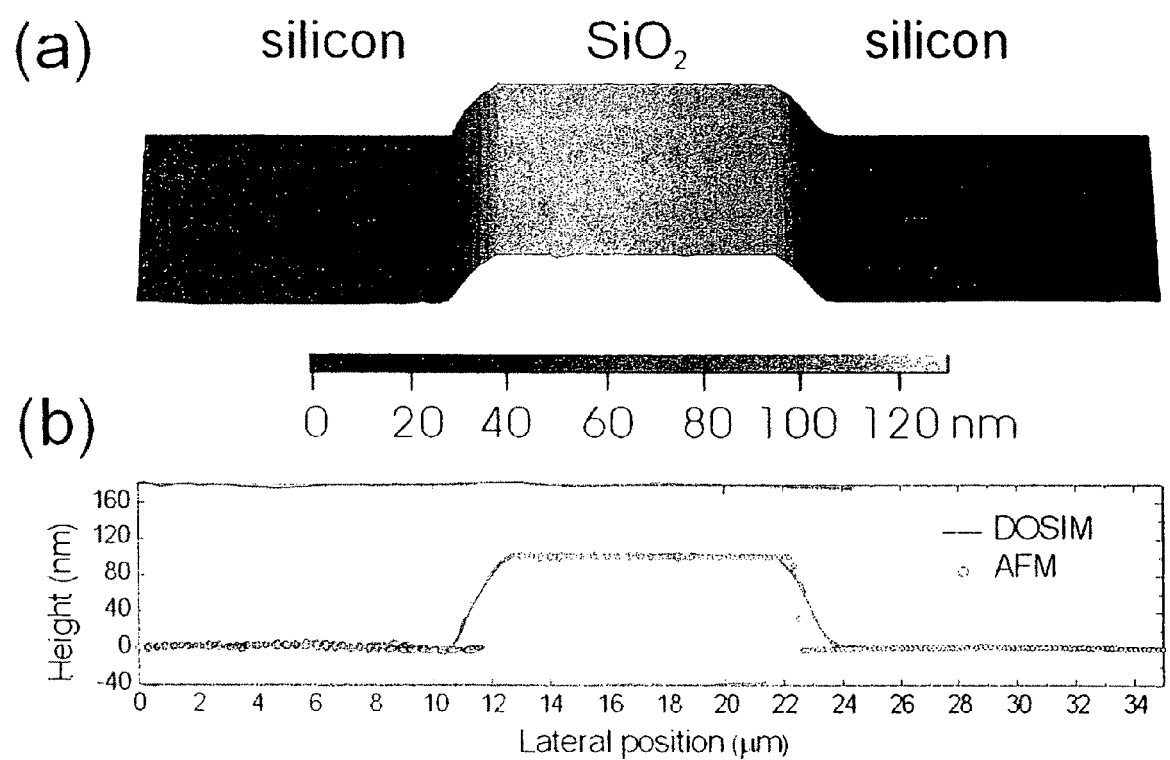
FIG. 4(a) is an illustration of the topography of a 12-μm-wide $SiO_2$ stripe grown on a Si substrate measured by the DOSIM system of FIG. 2(a)
FIG. 4(b) is a graphical plot of profiles of the $SiO_2$ stripe grown on a Si substrate measured by the DOSIM system of FIG. 2(a) in comparison to the measurement of the stripe by atomic force microscopy (AFM)

The advantages associated with the contemplated embodiments of the method and DOSIM system of the invention can be appreciated by, for example, measuring the n and d of a 12-μm-wide SiO₂ stripe deposited on Si. FIG. 4(a) is an illustration of the topography of such a 12-μm-wide SiO₂ stripe grown on a Si substrate measured using the DOSIM system of the present invention. Here, the refractive index $n_3$ of Si substrate is 3.947-0.026j at 600 nm, as measured by a conventional ellipsometer, such as model number SpecEI-2000-VIS, manufactured by Mikropack GmbH.

FIG. 4(b) is the graphical plot of profiles of the SiO₂ stripe grown on the Si substrate as measured by the DOSIM system of FIG. 2(a) in comparison to the measurement of the SiO₂ stripe using atomic force microscopy (AFM). Here, the thickness of such a stripe is 103.3±1.1 nm, which coincides closely with the result that is obtained using AFM. However, as shown in FIG. 4(b) the measurement results with respect to the edges of the SiO₂ stripe do not coincide. This is because the lateral resolution of AFM is much better than that of DOSIM. Moreover, the average index of such a SiO₂ stripe measured in accordance with the invention is 1.465±0.003, while the index of another area coated by SiO₂ on the same Si substrate as measured by the ellipsometer at the same wavelength is 1.468. The errors associated with the DOSIM measurement are caused mainly by the noise within the signal of the CCD camera. A signal-to-noise ratio of 200, which is a typical value for common digital CCD cameras, will cause an uncertainty of approximately 1% for the calculated thickness and approximately 0.1% for the refractive index.

Figure 5:
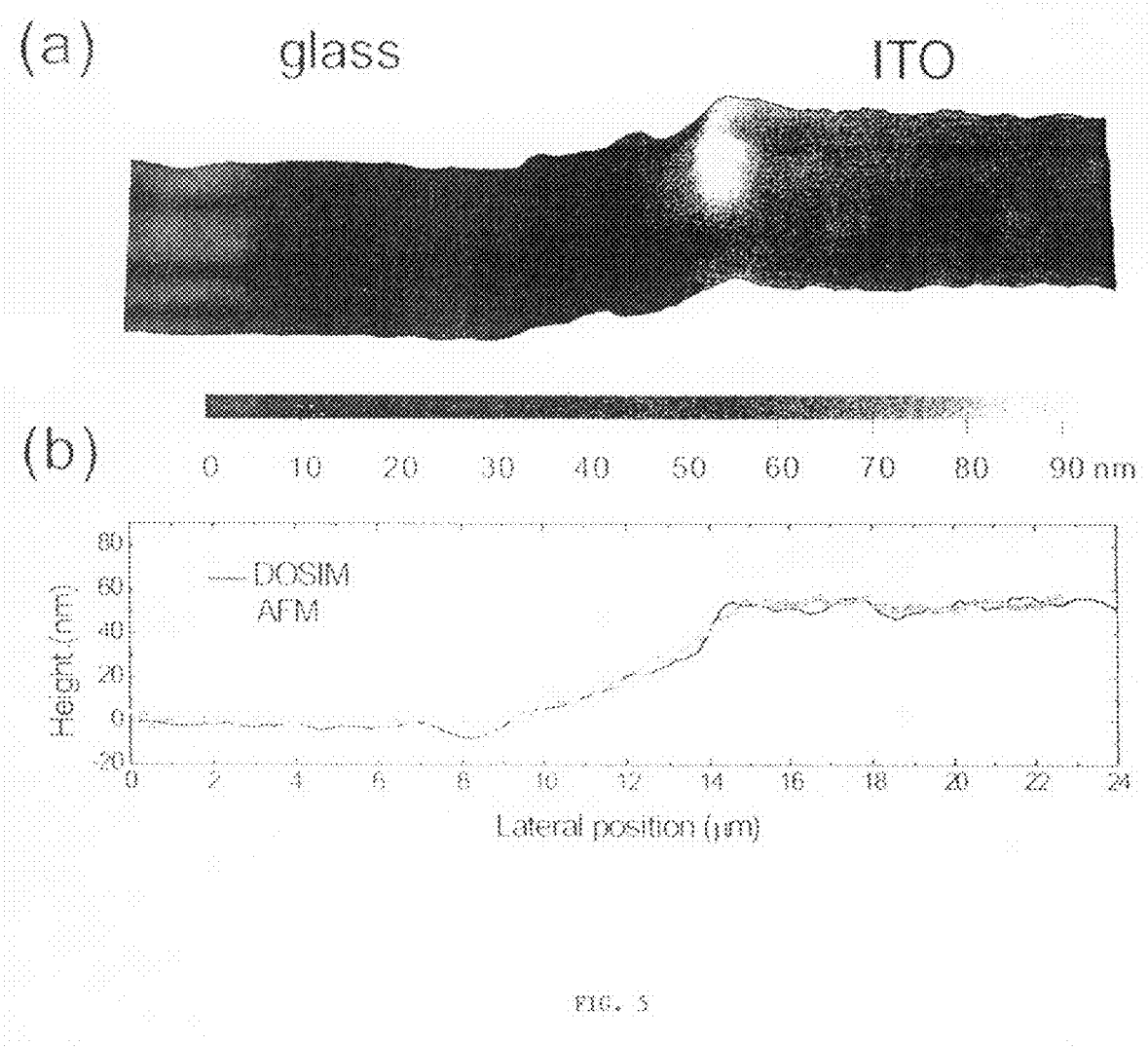
FIG. 5(a) is an illustration of the topography of an indium-tin-oxide (ITO) thin-film grown on a glass substrate measured by the DOSIM system of FIG. 2(a)
FIG. 5(b) is a graphical plot of the profiles of an ITO film measured by the DOSIM of FIG. 2(a) in comparison to the measurement of the film using AFM.

In an embodiment of the invention, the contemplated method and DOSIM system of the invention is implemented for substrates having low reflectivity. For example, a specimen is created by coating an indium-tin-oxide (ITO) film on glass ($n_3$=1.514). FIG. 5(a) is an illustration of the topography of such an indium-tin-oxide (ITO) thin-film grown on a glass substrate that is measured in accordance with the contemplated method and DOSIM system of the invention. FIG. 5(b) is a graphical plot of the profiles of such an ITO film measured by the DOSIM of FIG. 2(a) in comparison to the measurement of the film using AFM. Here, the refractive index and thickness measured by the DOSIM system are 1.79±0.018 and 60.3 nm, respectively. In contrast, the results obtained by the ellipsometer are n=1.816 and d=58.1 nm. The sub-micrometer lateral resolution of the DOSIM system of the contemplated embodiments permits the surface roughness of the ITO film to be obtained, which is not possible by using conventional ellipsometry. Here, the roughness of the ITO film measured by DOSIM and AFM is ±4.3 nm and ±2 nm respectively.

In another aspect of the invention, it is essential in the field of interferometry to avoid a 2π phase-wrapping ambiguity when working on thick films. Consequently, in accordance with the present invention, a 300-nm-thick SiO₂ film (e.g., δ>2π) is coated on Si and its index and thickness is measured using the DOSIM system of the invention. Here, a 20× microscope objective with a 0.4 NA is used to achieve a larger depth of focus.

Figure 6:
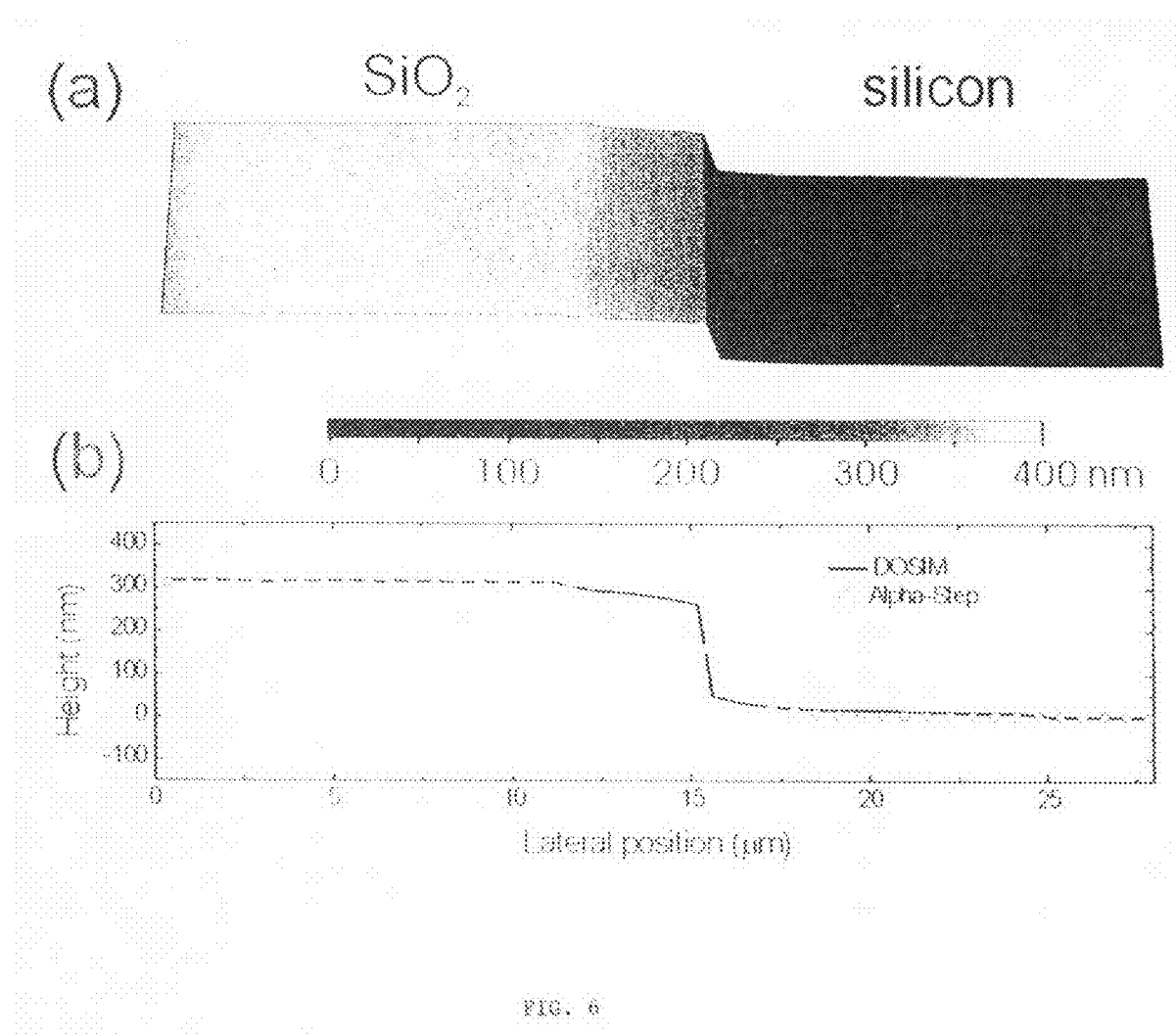
FIG. 6(a) is an illustration of the topography of a 300-nm $SiO_2$ film grown on a Si substrate measured by the DOSIM system of FIG. 2(a)
FIG. 6(b) is a graphical plot of the profiles of the $SiO_2$ film measured by DOSIM system of FIG. 2(a) in comparison to the measurement of the stripe using a surface profiler.

FIG. 6(a) is an illustration of the topography of such a 300-nm SiO₂ film grown on a Si substrate measured by the DOSIM system in accordance with the present invention. Here, the lateral resolution of the film at this objective that can be obtained is ~1 μm. Owing to the larger lateral resolution, the measurement of thickness is compared to the results obtained by a stylus surface profiler, such as a KLA Tencor, Alpha-Step IQ rather than the AFM.

FIG. 6(b) is a graphical plot of the profiles of the SiO₂ film measured by DOSIM system in comparison to the measurement using the surface profiler. Here, the n and d measured by the DOSIM system are 1.455±0.002 and 317.8±0.6 nm, respectively. As shown in FIG. 6(b), the thickness measurement obtained using DOSIM system of the present invention also coincides with the measured thickness that is obtained by the surface profiler. In contrast, the average n and d of this SiO₂ film when measured by the ellipsometer is 1.456 and 309 nm. Consequently, the measured results obtained in accordance with the method and DOSIM system of the invention indicates and provides correct measurements of thick films without the 2π phase-wrapping ambiguity.

The method in accordance with the invention is comprised of the following steps. An optical system is used to achieve optical sectioning, such as scanning confocal microscopy, non-scanning wide-field optical sectioning microscopy, or other image processing that can obtain an optically sectioned axial response curve. The optical system is used to measure the light reflected from the thin-film sample by using an optical element having a high numerical aperture (NA). Here, the lateral resolution can be estimated as 0.61λ/NA, where λ is the wavelength of the illumination light. It is possible for the optical element having the high numerical aperture to be either of an objective lens, a Fresnel zone plate, a graded-index lens, or other optical elements having a high numerical aperture.

In accordance with the method of the invention, the optical system uses a narrow-band light source. Here, the bandwidth of the light source must be sufficiently narrow such that the reflection light from the upper and lower interfaces of the thin-film to be measured can interfere. That is, the bandwidth of the light source must be sufficiently narrow such that the coherence length of the light is longer than the possible largest thickness of the thin-film. In the preferred embodiment, the coherence length is defined by $\lambda^2/\Delta\lambda$, where $\Delta\lambda$ is the bandwidth of illumination light. In addition, the narrow-band light source can be a laser, or a narrow-bandwidth component selected from a white-light source by using a monochromator or interference filters, or other light sources with a narrow bandwidth.

The thin-film to be measured is placed in the linear region of the optically sectioned axial response curve. In this region, the intensity of reflection light is determined by the position of the thin-film, the refractive indices of the thin-film and its substrate, and the interference effect from the upper and lower interfaces of the thin-film.

An optical detector is used to record the intensity of reflection light as the sample is placed in the linear region. Here, the detection can occur point-by-point, which is achieved by using a single detector, or by forming an image of the sample by using a array of detectors. The optical detector can be a photodiode, a photo-multiplier tube (PMT), a photodiode array, a charge-couple device (CCD) or complementary metal-oxide-semiconductor (CMOS) camera, or any other photo-detection instruments.

In order to calculate the thickness and refractive index of the thin-film, at least two measurements in the linear region of the axial response curve are performed to obtain two or more independent intensity equations. Here, the two measurements in the linear region of the axial response curve that are performed to obtain the two or more independent intensity equations can be performed by establishing one measurement in the linear region while the other is established on the focal plane, i.e., top/peak, of the axial response curve. Moreover, the two measurements in the linear region can be performed at two different positions in the linear region of the axial response curve. It is also possible to obtain the two or more independent intensity equations such that the two measurements in the linear region of the axial response curve is performed by obtaining two different polarization characteristics of the light source if the source provides polarized light. Alternatively, the two measurements in the linear region of the axial response curve can be performed by obtaining two different phase characteristics of the light source.

Next, the two or more equations are used to calculate the thickness d and refractive index n of the thin-film by numerical methods. It should be understood that the accuracy of the thickness and refractive index obtained in accordance with the method of the invention is determined by the signal-to-noise ratio of the measured intensity.

The contemplated method and DOSIM system of the present invention permits the simultaneously measurement of refractive indices and thicknesses of transparent thin-films. The contemplated embodiments of the invention permit the use of a microscope objective in the normal direction as the probe, i.e., in the direction perpendicular to the latitudinal surface of the film, in cases where the lateral resolution can easily be smaller than 1 µm in the visible spectral region. In comparison to conventional ellipsometry, the differences in refractive index and thickness of a 100-nm $SiO_2$ film measured in accordance with the method and DOSIM system of the invention are within 0.2% and 1.1 nm, respectively. Moreover, the method and system permit the achievement of correct measurements when an ITO film is grown on a transparent glass substrate.

Setup of the contemplated DOSIM system is based on a conventional optical microscope. As a result, deployment of the method and system in production lines is readily achieved. Moreover, it is also contemplated that a set of narrow-band filters with a white-light source can be used to develop the disclosed the method and DOSIM system of the invention into a spectroscopic diagnosis tool for versatile thin-film characterizations.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

[1] R. M. A. Azzam and N. M. Bashara, Ellipsometry and Polarized Light. (North-Holland, Amsterdam, 1987).

[2] A.-H. Liu, P. C. Wayner, Jr., and J. L. Plawsky, "Image scanning ellipsometry for measuring nonuniform film thickness profiles," Appl. Opt. 33, 1223-1229 (1994).

[3] A. Albersdorfer, G. Elender, G. Mathe, K. R. Neumaier, P. Paduschek, and E. Sackmann, "High resolution imaging microellipsometry of soft surfaces at 3 µm lateral and 5 Å normal resolution," Appl. Phys. Lett. 72, 2930-2932 (1998).

[4] S. Otsuki, K. Tamada, and S.-I. Wakida, "Two-dimensional thickness measurements based on internal reflection ellipsometry," Appl. Opt. 44, 1410-1415 (2005).

[5] Q. Zhan and J. R. Leger, "High-resolution imaging ellipsometer," Appl. Opt. 41, 4443-4450 (2002).

[6] M. A. A. Neil, R. Juskaitis, and T. Wilson, "Method of obtaining optical sectioning by using structured light in a conventional micrope," Opt. Lett. 22, 1905-1907 (1997).

[7] C.-H. Lee and J. Wang, "Noninterferometric differential confocal microscopy with 2-nm depth resolution," Opt. Commun. 135, 233-237 (1997).

[8] C. H. Lee, H.-Y. Mong, and W.-C. Lin, "Noninterferometric wide-field optical profilometry with nanometer depth resolution," Opt. Lett. 27, 1773-1775 (2002).

[9] C.-C. Wang, J.-Y. Lin, and C.-H. Lee, "Membrane ripples of a living cell measured by non-interferometric widefield optical profilometry," Opt. Express 13, 10665-10672 (2005).

[10] C.-W. Tsai, C.-H. Lee, and J. Wang, "Deconvolution of local surface response from topography in nanometer profilometry with a dual-scan method," Opt. Lett. 24, 1732-1734 (1999).

What is claimed is:

1. A method for measuring a transparent thin-film to determine refractive indices n and thicknesses d of the thin-films, comprising:

measuring the transparent thin-film to obtain an optically sectioned axial response curve;

translating the transparent thin-film along an optical axis until intensity from the transparent thin-film is within the linear region of the optically sectioned axial response curve;

performing at least two measurements in the linear region of the axial response curve to obtain two or more independent intensity relationships; and calculating a refractive index and thickness of the thin-film based on the independent intensity relationships.

2. The method of claim 1, wherein optical sectioning is performed with one of a scanning confocal microscope and a non-scanning wide field optical sectioning microscope.

3. The method of claim 1, wherein an optical system is used to measure light reflected from the thin-film by using an optical element having a aperture (NA) of approximately 0.55.

4. The method of claim 3, wherein a lateral resolution of the optical element is approximately $0.61\lambda/0.55$, wherein $\lambda$ is the wavelength of illumination light.

5. The method of claim 4, wherein the optical element is one of an objective lens, a Fresnel zone plate and a graded-index lens.

6. The method of claim 3, wherein the optical system uses a narrow-band light source.

7. The method of claim 6, wherein the bandwidth of the light source is sufficiently narrow such that reflection light from upper and lower interfaces of the thin-film to be measured can interfere.

8. The method of claim 6, wherein the bandwidth of the light source is sufficiently narrow such that the coherence length of the illumination light is longer than a largest possible thickness of the thin-film.

9. The method of claim 8, wherein the coherence length is $\lambda^2/\Delta\lambda$, where $\lambda$ is the wavelength and $\Delta\lambda$ is the bandwidth of illumination light.

10. The method of claim 6, wherein the narrow-band light source is one of a laser and a narrow-bandwidth component selected from a white-light source using a monochromator or interference filters.

11. The method of claim 1, wherein the intensity of reflection light, with the thin-film in the linear region of the optically sectioned axial response curve, is determined by at least one of a position of the thin-film, the refractive indices of the thin-film and its substrate and an interference effect from upper and lower interfaces of the thin-film.

12. The method of claim 1, said translating step comprising the step of recording intensity of reflection light via an optical detector while the thin-film is translated along the optical line within the linear region.

13. The method of claim 12, wherein said recording comprises at least detecting the intensity of reflection light point-by-point.

14. The method of claim 13, wherein said detection is achieved by using a single detector or by forming an image of the thin-film by using an array of detectors.

15. The method of claim 12, wherein the optical detector is one of a photodiode, a photo-multiplier tube (PMT), a photodiode array, a charge-couple device (CCD) and complementary metal-oxide-semiconductor (CMOS) camera.

16. The method of claim 1, wherein said performing step comprises establishing one measurement in the linear region of an axial response curve and establishing another measurement on the focal plane of the axial response curve.

17. The method of claim 16, wherein the focal point of the axial response curve is the peak of the curve.

18. An optical system for measuring a transparent thin-film to determine refractive indices n and thicknesses d of the thin-films, wherein the system is configured to implement a program code stored in a module to:
measure the transparent thin-film to obtain an optically sectioned axial response curve;
translate the optical thin-film along an optical axis until intensity from the optical thin-film is within the linear region of the optically sectioned axial response curve;
perform at least two measurements in the linear region of the axial response curve to obtain two or more independent intensity relationships; and
calculate a refractive index and thickness of the thin-film based on the independent intensity relationships.

19. The system of claim 18, wherein optical sectioning comprises one of scanning confocal microscopy and non-scanning wide field optical sectioning microscopy.

20. The system of claim 18, wherein the optical system measures light reflected from the thin-film by using an optical element having a high numerical aperture (NA).

21. The system of claim 20, wherein a lateral resolution of the optical element is approximately $0.61\lambda/NA$, wherein $\lambda$ is illumination wavelength of light.

22. The system of claim 21, wherein the optical element is one of an objective lens, a Fresnel zone plate and a graded-index lens.

23. The system of claim 18, wherein the optical system includes a narrow-band light source.

24. The system of claim 23, wherein the bandwidth of the light source is sufficiently narrow such that reflection light from upper and lower interfaces of the thin-film to be measured can interfere.

25. The system of claim 23, wherein the bandwidth of the light source is sufficiently narrow such that the coherence length of the illumination light is longer than the largest possible thickness of the thin-film.

26. The system of claim 25, wherein the coherent light is $\lambda^2/\Delta\lambda$, where $\lambda$ is the wavelength and $\Delta\lambda$ is the bandwidth of illumination light.

27. The system of claim 23, wherein the narrow-band light source is one of a laser and a narrow-bandwidth component selected from a white-light source using a monochromator or interference filters.

28. The system of claim 18, wherein the intensity of reflection light, with the thin-film in the linear region of the optically sectioned axial response curve, is determined by at least one of a position of the thin-film, the refractive indices of the thin-film and its substrate and an interference effect from upper and lower interfaces of the thin-film.

29. The system of claim 18, wherein placement of the optical thin-film in the linear region of the optically sectioned axial response curve comprises recording an intensity of reflection light via an optical detector while the thin-film is placed in the linear region.

30. The system of claim 29, wherein said recording comprises at least detection of the intensity of reflection light, point-by-point.

31. The system of claim 30, wherein said system includes one of a single detector and array of detectors.

32. The system of claim 29, wherein the optical detector is one of a photodiode, a photo-multiplier tube (PMT), a photodiode array, a charge-couple device (CCD) and complementary metal-oxide-semiconductor (CMOS) camera.

33. The system of claim 18, wherein said performance comprises establishment of one measurement in a linear region of an axial response curve and the establishment of another measurement on the focal plane of the axial response curve.

34. The system of claim 33, wherein the focal point of the axial response curve is the peak of the curve.

35. A method for measuring an optical thin-film to determine refractive indices n and thicknesses d of the thin-films, comprising:
measuring the optical thin-film to obtain an optically sectioned axial response curve;

translating the optical thin-film along an optical axis until intensity from the optical thin-film is within the linear region of the optically sectioned axial response curve;

performing at least two measurements in the linear region of the axial response curve to obtain two or more independent parameters; and calculating a refractive index and thickness of the thin-film based on the independent parameters.

36. The method of claim 35, wherein the independent parameters comprise one of polarization and phase relationships.

* * * * *